Figure 3:
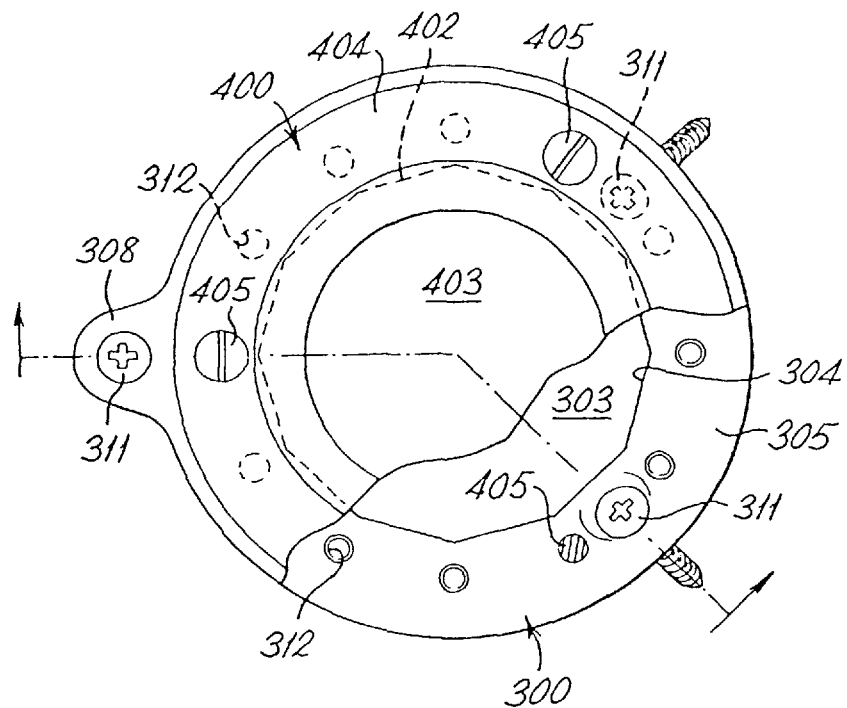

United States Patent

Church

[11] Patent Number: 5,879,399
[45] Date of Patent: Mar. 9, 1999

[54] ENDOPROSTHETIC BONE JOINT DEVICES

[75] Inventor: John Christian Tracey Church, Bourne End, England

[73] Assignee: British Technology Group Ltd., London, England

[21] Appl. No.: 456,710

[22] Filed: Jun. 1, 1995

Related U.S. Application Data

[63] Continuation of Ser. No. 21,609, Mar. 3, 1987, which is a continuation of Ser. No. 482,708, Apr. 6, 1983, abandoned.

[30] Foreign Application Priority Data

Apr. 7, 1982 [GB] United Kingdom .................... 8210272

[51] Int. Cl.[6] ......................................... A61F 2/34
[52] U.S. Cl. ............................................... 623/22
[58] Field of Search .................. 623/16, 18, 19, 623/20, 22, 23, 66

[56] References Cited

U.S. PATENT DOCUMENTS

| | | | |
|---|---|---|---|
| 3,584,318 | 6/1971 | Scales et al. .............................. | 623/22 |
| 3,903,549 | 9/1975 | Deyerle ..................................... | 623/22 |
| 3,996,625 | 12/1976 | Noiles ....................................... | 623/22 |
| 4,172,296 | 10/1979 | D'Errico ................................... | 623/22 |

FOREIGN PATENT DOCUMENTS 2950536  2/1981  Germany .................................. 623/22

*Primary Examiner*—David Isabella
*Attorney, Agent, or Firm*—Cushman Darby & Cushman IP Group of Pillsbury Madison & Sutro LLP

[57] ABSTRACT

An endoprosthetic acetabular component of overall cup form is improved by the provision of an outer part (100; 300; 500) for securement to bone and a plurality of inner parts (200; 400; 600) individually selectively interconnectable with the outer part in like manner but providing a dished articulating surface (203; 403; 603) in respectively different predetermined positions varying in depth and/or inclination. The interconnection is preferably rotatably adjustable relative to the cup mouth, suitably by the provision of mutually complementary indented/detented surface formations (104, 202; 304,402; 505,607) on the parts. The outer part may also be selectable from a range adapted to respectively different manners of securement to bone.

1 Claim, 3 Drawing Sheets

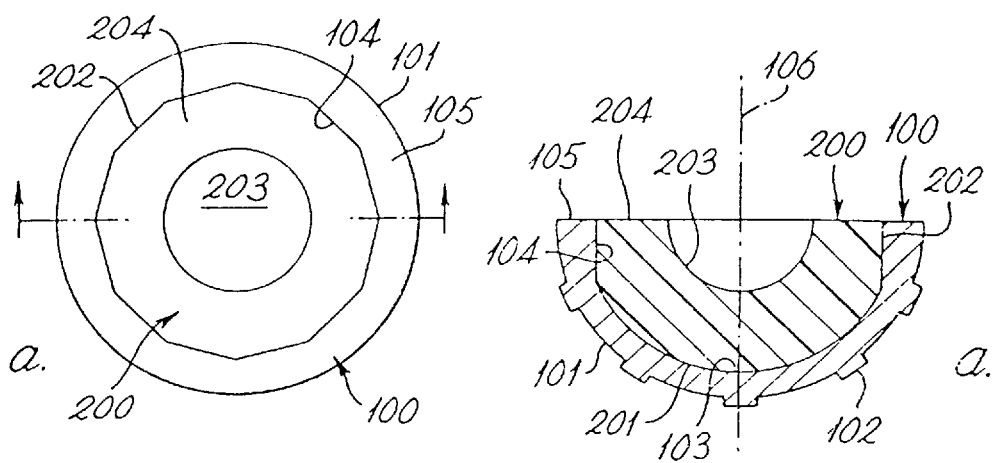
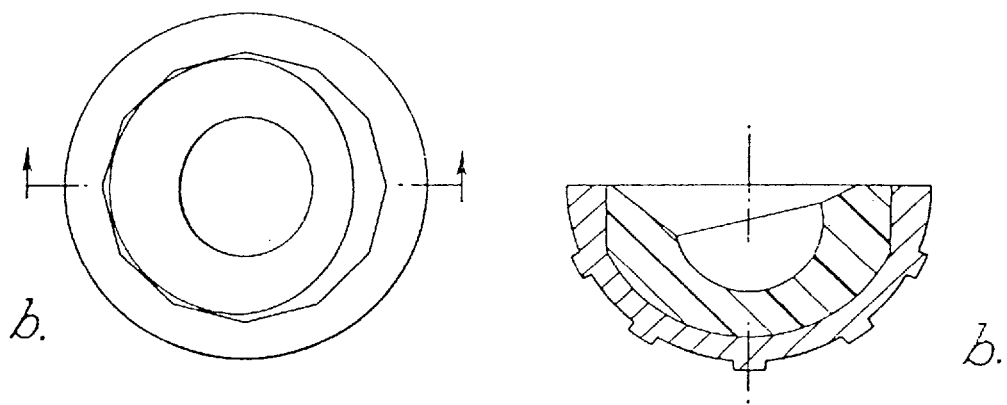
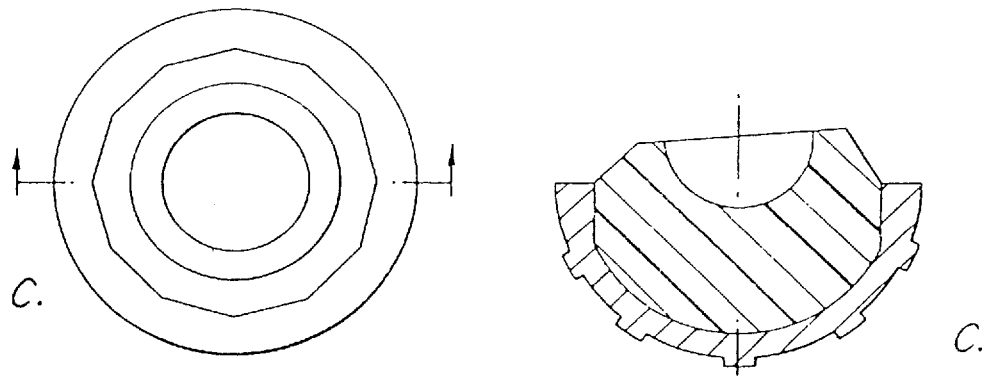
Fig. 1    Fig. 2

ENDOPROSTHETIC BONE JOINT DEVICES

This is a continuation of application Ser. No. 07/021,609, filed Mar. 3, 1987, which is a continuation of 06/482,708 filed Apr. 6, 1983 now abandoned.

This invention concerns endoprosthetic bone joint devices and more particularly such devices including a component of overall cup form to replace the acetabulum in the hip joint.

Present day acetabular cup components represent the result of several decades of clinical experience and a yet longer period of trial and development, but the use of such components is nevertheless not without difficulties.

A general difficulty is that an optimum result requires accuracy in the positioning of the component in the pelvis, but such positioning is hindered by the fact that the component has a preset overall geometry while the pelvis will vary in shape between individual patients and so give no absolute spacial frame of reference, and current securement techniques employing fast-curing acrylic bone cement give little scope for adjustment after the component has been first located. The component is usually introduced with a single smooth action to ensure that cement is evenly distributed between it and the bone, and the component is thereafter held steadily, without angular or lateral movement, while the cement is curing in order to avoid the creation of voids or other weaknesses in the securement. In practice therefore the initial positioning of the component is definitive and the attainment of an optimum result accordingly requires skill and care, while the later consequences of failure include undue component wear and/or dislocation.

Even if skill and care are exercised, there is still a difficulty in that optimum positioning of the outer and inner surfaces of the component are respectively determined by the requirements of securement and articulation but, because these requirements can varyingly differ from one patient to another, attainment of both optima is often compromised by a component of preset overall geometry.

An object of the present invention is to reduce these difficulties and to this end there is provided an endoprosthetic acetabular component of overall cup form comprising an outer part and a plurality of inner parts individually selectively co-operable with said outer part, the outer part being adapted for securement to bone, and each inner part being interconnectable with said outer part in like manner and defining a dished articulation surface having a respectively different predetermined position relative to said outer part when connected therewith.

Preferably the inner parts afford a range of articulation surface positions varying in depth and inclination relative to the outer part.

Also, it is preferred that the outer and inner parts are rotatably adjustably interconnectable relative to the mouth of the overall cup form.

The benefit of the proposed device relative to the above-mentioned difficulties is that the outer part can be secured to the bone separately with a fuller attention being paid to the requirements of securement in terms of the geometry and mechanical condition of the bone, and thereafter an appropriate one of the inner parts can be selectively interconnected to locate its dished surface in the position which is judged to be best for the purposes of articulation.

The outer part can take various forms to allow for securement to bone in accordance with established or future techniques. For example, the part can have an outermost surface with a ribbed-and-grooved or other relieved configuration for cooperation with bone cement, or the part can be apertured for the passage of screws therethrough. Indeed the outer part can itself be made available in such different forms interconnectable with the same range of inner parts in like manner to allow a choice of securement technique best suited to a bone when exposed during surgery.

Variation is also possible in the adaptation for interconnection between the outer and inner parts. It is presently preferred that such adaptation involve mutually complementary indented and detented formations on the outer and inner parts. In initially conceived forms of the invention such formations were applied to the interior and exterior surfaces respectively of the outer and inner parts. These initial forms typically involve prismatic surface forms of polygonal or other non-circular cross-sectional shape. However it is now thought advantageous to apply the complementary formations to rim surfaces of the outer and inner parts in order to facilitate associated machining or other fabrication operations. More recently conceived forms of the invention in fact typically involve castellated rim surface formations.

Figure 4:
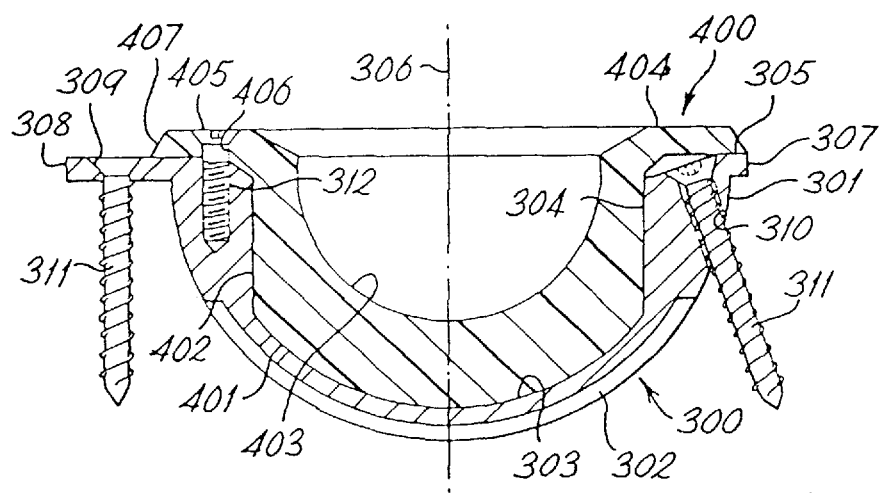
Figure 5:
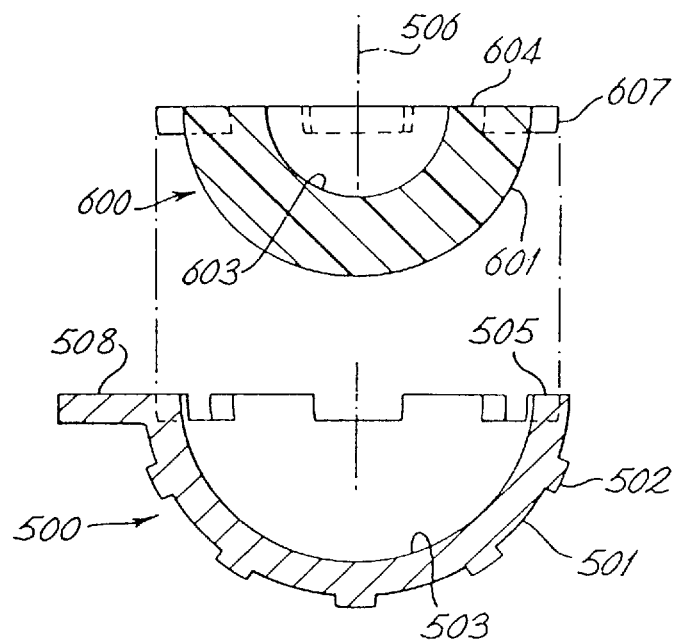
Figure 6:
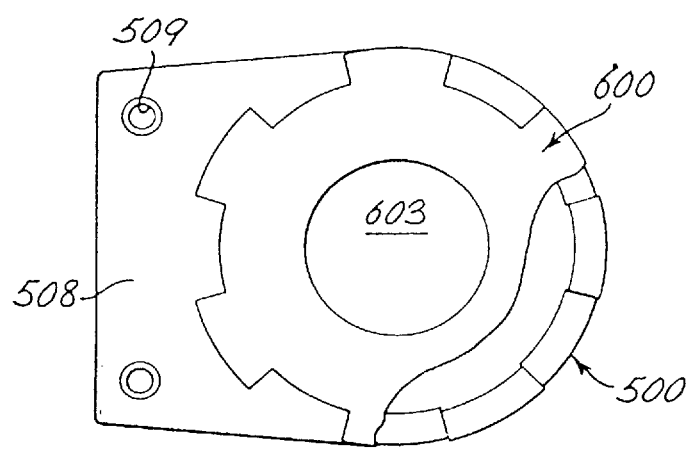

In order that the invention may be clearly understood and readily carried into effect, it will now be more fully described, by way of example, with reference to the accompanying drawings in which:

FIGS. 1 and 2 respectively illustrate in plan and cross-sectional views one embodiment of an acetabular cup component according to the present invention;

FIGS. 3 and 4 similarly illustrate a further such embodiment, but with the inner component part partially cut away plan view; and FIGS. 5 and 6 similarly illustrate another such embodiment, also with the inner part partially cut away in plan view and with the outer and inner parts disengaged in side view.

FIGS. 1 and 2 are in fact each in three parts (a), (b) and (c) illustrating the use of respectively different inner parts of a range thereof for connection with a common outer component part. Notwithstanding these differences, it is appropriate to employ common reference numerals throughout these figures.

The principal component parts, the outer and inner parts, are respectively denoted at 100 and 200 and each is of generally cup form.

The outer part 100 has a main exterior surface 101 which is basically spherically shaped, but is supplemented by the provision of raised portions 102, such as annular ribs, to form a relieved surface configuration. The interior surface of the part 100 has an innermost portion 103 which is spherically shaped concentrically with the exterior surface 101, and a remaining prismatically shaped portion 104 which extends to the rim surface 105 and is of regular polygonal cross-sectional shape.

The overall shaping of the outer part is symmetrical about the longitudinal axis 16 of the prismatic surface portion 104.

The inner part 200 has a main exterior surface with spherically and prismatically shaped portions 201 and 202 complementary to surface portions 103 and 104 of the outer part 100, whereby the inner part can be engaged in the outer part as shown. The remaining surface areas of the inner part comprise a substantially hemispherical interior surface 203 and rim surface 204, and these surfaces vary from one inner part to another within a range thereof.

These surface variations in the inner part involve, as noted above, two basic factors.

A first factor is that of the depth of the surface 203. There will normally be at least three positions, namely, a normal or standard one in which the surface 203 is typically concentric with the spherically shaped portion 201 of the exterior surface, and low and high positions in which the surface 203 is respectively more and less deeply located.

The second variant factor is that of the inclination of the surface 203 relative to the axis 106. Typically there can be five different angles such as 0°, 3°, 5°, 10° and 15°, or some other range up to a maximum of about 20°.

It will be appreciated that with variations such as just described there can be fifteen different inner parts to cater for different articulation requirements for a given outer part location in an individual pelvis. FIGS. 1 and 2 show at (a), (b) and (c) three examples of such parts, namely, standard depth at 0° or neutral inclination, low depth at 15° inclination, and high depth at 5° inclination. These examples also serve to show associated variations in the form of the rim surface 204.

It is to be noted that, in addition to these variations in inner part geometry, each such part can be located in as many different positions within the outer part as there are faces to the prismatic surface shaping at 104 and 202 simply by appropriate rotational positioning of the inner part during engagement with the outer part. This is relevant, of course, to the inclined rather than the neutral inner parts. It is thought, at present, adequate to provide twelve rotational positions successively spaced by 30°.

Use of the embodiment of FIGS. 1 and 2 is largely self-evident from the foregoing description.

The outer part 100 is first secured in the acetabulum after suitable exposure and preparation of the bone, such securement taking the fullest account of the bone geometry and condition to ensure optimal engagement within sound bone material. In the present instance securement is to involve the currently conventional usage of bone cement as a gap-filling medium which forms a mechanical lock with the surface 101 and raised surface portions 102 on the one hand and with the pores of the prepared bone and cavities prepared therein on the other hand.

Thereafter the inner part 200 is selected which, when engaged in the secured outer part 100, is judged to have its surface 203 best located to serve the purposes of articulation in association with a femoral head replacement providing a ball complementary with the surface 203. This selection will involve consideration of the depth, inclination and rotation angle of the surface 203 and will normally be established by the use of trial inner parts which are readily engageable and withdrawable from the secured outer part. Once this selection is made, a replacement inner part of the corresponding configuration is secured in the outer part, suitably by press fitting.

The embodiment of FIGS. 3 and 4 is sufficiently similar in many respects to that just described, not least in the geometrical variations for the interior surface of the inner part, that it is only necessary for one example to illustrate the differences. Also, it is convenient to employ the same reference numerals for corresponding features between the two embodiments, but with increase of the hundreds digit to distinguish the second embodiment so that the outer and inner parts are respectively denoted as 300 and 400.

A first difference in FIGS. 3 and 4 is that securement of the outer part 300 does not rest on the use of bone cement alone, although a grooved structure, with ribs 302, is provided for this purpose over the lower part of the exterior surface 301. As an additional feature, the outer part rim is radially outwardly lipped at 307 and part of the lip continues into a lug 308 which is apertured at 309 to allow screw securement to underlying bone. Also, at locations opposed to the lug 308, the side wall of the outer part is obliquely bored at 310 from the rim to the exterior surface to allow additional screw securement to additional bone. In each case the screw-receiving bores are suitably counterbored and/or countersunk so that the heads of the associated screws 311 are not proud of the outer part rim.

A further difference is that the inner part 400 is secured to the outer part by screws 405 in addition, or as an alternative, to press fitting. In this connection the outer part has circumferentially uniformly spaced tapped bores 312 around its rim, and the inner part has three similarly located countersunk bores 406 which register with bores 312 at any position of rotational adjustment. It will be noted that the inner part rim is lipped at 407 to overlie that of the outer part and to accomodate the bores 406.

The embodiment of FIGS. 5 and 6 also only requires one example to illustrate its different features and, conveniently again, the same reference numberal sequence is used but with the outer and inner parts respectively denoted as 500 and 600.

The main difference in this embodiment is the provision of mutually complementary castellated formations in the rim surface 505 of the outer part and in the rim lip 607 of the inner part. These formations are uniformly circumferentially distributed to allow rotationally selective engagement of the outer and inner parts in place of the prismatic surface portions of the previous embodiments. In the present case the interior and exterior surfaces 503 and 601 of the outer and inner parts can be wholly spherically shaped, as shown.

A further difference in this third embodiment is that the outer part has a lug 508 apertured at 509 for screw securement to bone, but the lug is widened relative to that of FIGS. 3 and 4.

While the invention has been described in more detail with reference to the illustrated examples, this is not intended to be exhaustive in respect of possible variations. There are in fact a number of facets of the invention where further variation is possible.

Securement of the outer cup is one such facet. Reference has already been made to the possiblity of using bone cement and/or screws, but use may be made of any other securement technique. One such technique can involve so-called in-growth by the use of porous or functionally equivalent formations into which fibrous material grows and then ossifies. Another possiblity contemplated for study in further development of the invention is that primary securement by screws or other force-fitted elements may be enhanced by the packing of bone chips or paste, suitably prepared from the patient's excised femoral head, to fill voids in the acetabular site and between it and the outer part. This last possiblity amounts in general terms to a bone grafting technique.

Also, in connection with securement of the outer part, variation can be exercised in respect of external shaping as is already evident from the variable provision of lugs and other elements. Another such variation contemplated for use with the invention is the provision of a transversely elongated ovalate shaping in place of the generally spherically shaped exterior surface to conform better to the natural acetabular shaping. The relevant ovalate shaping may reduce any tendency for migration of the component in the pelvis as is sometimes witnessed during revision surgery. Again, it is not essential for the purposes of the present invention that the outer part be wholly cup-shaped: a generally annular form may suffice.

Another facet open to considerable variation in detail is the adaptation for, and the mode of, interconnection between the outer and inner parts. Alternatives in adaptation are already evident from the examples of prismatic and castellated surface formations, but many other possibilities exist for suitable indented/detented formations. It will generally be appropriate to deploy any such formations uniformly circumferentially, but this is not essential. Thus, it can be adequate to provide a discrete rotational adjustment capability over less than 360° for situations where the overall orientation of the component is predictable in general terms, such predictably resulting, for example, from the use of an ovalate exterior shaping. Again, it is not essential that the outer and inner parts inherently comprise mutually complementary formations: for example the embodiment of FIGS. 3 and 4 could be rotatably adjustably connected by way of the outer part bores 312 and the co-operating screws 405 passing through the outer part.

Regarding the mode of interconnections: reference has been made to press fitting, but screw interconnection is also shown, as just mentioned, and another possibility can involve the use of a thin layer of bone cement on other bonding or gap-filling material. However, whatever the mode of interconnections, it is desirable that the inner part should be separable without undue difficulty, while leaving the outer part intact and secured to bone, against a possible future need for revision.

A further facet involves the position of the articulation surface of the inner part. As so far described in the illustrated embodiments this location is, even allowing for any inclination, generally central to the extent that the spherical centre of the relevant surface lies on the axis 106, 306 or 506. However, as an alternative, this centre can be translated from the axis in order to provide an increased wall thickness along the main line of load in use and, again, the preferred rotational adjustment facility has relevance to this feature.

Yet another facet for variation lies in the choice of materials for the device. On the basis of the materials most commonly used at present in endoprosthetic bone joint devices it is preferred that the outer and inner parts respectively be of metal such as stainless steel, chrome-cobalt alloy or titanium alloy, and plastics material such as ultra high molecular weight polyethylene. Such a combination will provide stable securement to bone and low friction articulation with an associated metal femoral component. However other materials such as cermaics are in current usage, and others are under trial and development, so that various suitable choices, will be possible.

I claim:

1. A system for forming a socket component for use in a ball-and-socket bone joint prosthesis, said system comprising:

a plurality of bearing elements each having an articulation surface for receiving a ball;

a fixation member adapted for securement to a bone and having a cavity for receiving any selected one of said bearing elements, said cavity having an opening defining a plane through which said one bearing element enters the cavity; and means for connecting said one bearing element to said fixation member in any one of a plurality of selectable orientations after such member has been attached to said bone, said plurality of orientations being mutually angularly displaced about an axis which is perpendicular to said plane and passes through said opening;

said connecting means comprising a set of tapped bores located about the cavity of the fixation member and at least one hole in a rim of each bearing element overlying the tapped bores, whereby screws placed through the holes and extending into the tapped bores enables placement of the bearing element in the cavity of the fixation member in any one of the said selectable orientations;

said articulation surface of at least a first one of said bearing elements being non-uniform about said axis when connected in said fixation member to provide a varying restraint against dislocation of said ball dependent on the direction of articulation; and said articulation surface of at least a second one of said bearing elements being uniform about said axis when connected in said fixation member to provide a uniform restraint against dislocation of said ball.

* * * * *